(12) United States Patent
Scaiano et al.

(10) Patent No.: US 6,903,340 B1
(45) Date of Patent: Jun. 7, 2005

(54) THIN FILM ANALYZER

(76) Inventors: Juan Cesar Scaiano, 2196 Ernard Crescent, Ottawa, Ontario (CA), K1J 6K6; John Francis Bohland Jr., 4901 Creekside Dr., New Bern, NC (US) 28562

( * ) Notice: Subject to any disclaimer, the term of this patent is extended or adjusted under 35 U.S.C. 154(b) by 238 days.

(21) Appl. No.: 10/278,967

(22) Filed: Oct. 22, 2002

Related U.S. Application Data
(60) Provisional application No. 60/336,460, filed on Oct. 23, 2001.

(51) Int. Cl.[7] .............................. G01N 1/00; H01L 21/68
(52) U.S. Cl. ............................................... 250/339.07
(58) Field of Search ........................ 250/339.09, 339.11, 250/341.1, 341.2, 341.4, 341.5, 341.8

(56) References Cited

U.S. PATENT DOCUMENTS

| | | | | |
|---|---|---|---|---|
| 4,203,799 A | * | 5/1980 | Sugawara et al. | ............ 117/85 |
| 4,647,172 A | * | 3/1987 | Batchelder et al. | ......... 396/569 |
| 4,823,009 A | * | 4/1989 | Biemann et al. | ......... 250/341.4 |
| 4,998,021 A | * | 3/1991 | Mimasaka | ............. 250/559.28 |
| 5,304,813 A | * | 4/1994 | De Man | ...................... 250/556 |
| 5,427,878 A | * | 6/1995 | Corliss | ........................ 430/30 |
| 5,452,953 A | * | 9/1995 | Ledger | ....................... 356/632 |
| 5,764,352 A | * | 6/1998 | Kappel et al. | ............... 356/225 |
| 5,982,166 A | * | 11/1999 | Mautz | ...................... 324/158.1 |
| 6,271,047 B1 | * | 8/2001 | Ushio et al. | .................. 438/14 |
| 6,275,297 B1 | * | 8/2001 | Zalicki | ....................... 356/496 |

* cited by examiner

*Primary Examiner*—David Porta
*Assistant Examiner*—Faye Polyzos
(74) *Attorney, Agent, or Firm*—John F. Bohland (57) ABSTRACT

A thin film analyzer capable of static and dynamic measurements is disclosed. The apparatus collects and analyzes spectral reflectance data as a function of time. It is especially useful for measuring the changing thickness of a transparent, organic thin film as it is dissolved by a solvent. The measurements can be made with small quantities of solvent, on the order of one milliliter, in small, localized areas on a coated substrate, thereby allowing multiple, independent measurements on each substrate with minimal consumption of solvent.

16 Claims, 7 Drawing Sheets

Prior Art

THIN FILM ANALYZER

CROSS REFERENCE TO RELATED APPLICATIONS

The present application claims priority based on currently pending provisional application 60/336,460 which was filed on Oct. 23, 2001 and is incorporated herein by reference.

BACKGROUND OF INVENTION

Several different types of currently available instruments may be used to measure the thickness and optical constants of a static thin film. Other systems are designed to dynamically monitor film thickness changes. Photoresist users, manufacturers, and raw material suppliers utilize both types of systems. In order to optimize raw materials and formulations they measure fundamental properties of the materials and simulate lithographic performance. In addition to the thickness and optical properties of thin polymer films, they need to measure the dissolution rates of the films in photoresist developers. The commercially available systems do not provide a cost effective solution to the needs of the photoresist designers and users. There exists a need for an inexpensive and reliable system that will perform both the static and dynamic functions in an expeditious and efficient manner.

Custom, noncommercial systems to measure dissolution rates of organic films have been used for years for testing photoresists and constituent polymers. The earliest systems were usually similar to the one shown in FIG. 1. A 632.8 nm HeNe laser 101 is used as a source of monochromatic radiation. The laser light is conducted by means of a first set of optical fibers in a bifurcated fiber optic cable 102 to the surface of a substrate 103 coated with a thin film of photoresist or polymer. The substrate is typically a silicon wafer as used in the manufacture of semiconductor devices. A fixture 104 is provided to maintain a near-normal angle of incidence between the substrate and the fiber optic cable while both are immersed in a container of developer 105. Reflected light is collected by a second set of fibers in the bifurcated cable and directed to an assembly 106 containing an optical filter and photodiode detector. The light emission from the fiber optic cable is not in the form of a narrow beam as originally emitted from the laser and, therefore, illuminates a relatively large area on the substrate. Given this broad area of illumination and the specular nature of the substrate, an image of the emitting fibers is reflected onto the collecting fibers without a need for critical alignment. In order to avoid interference from ambient light, a 632.8 nm interference filter may be included in the optical path before the detector. The photodiode signal is sent to an amplifier 107 and a strip chart recorder 108. This system is capable of collecting reflectance data from a single point on a substrate at a single wavelength.

Figure 1:
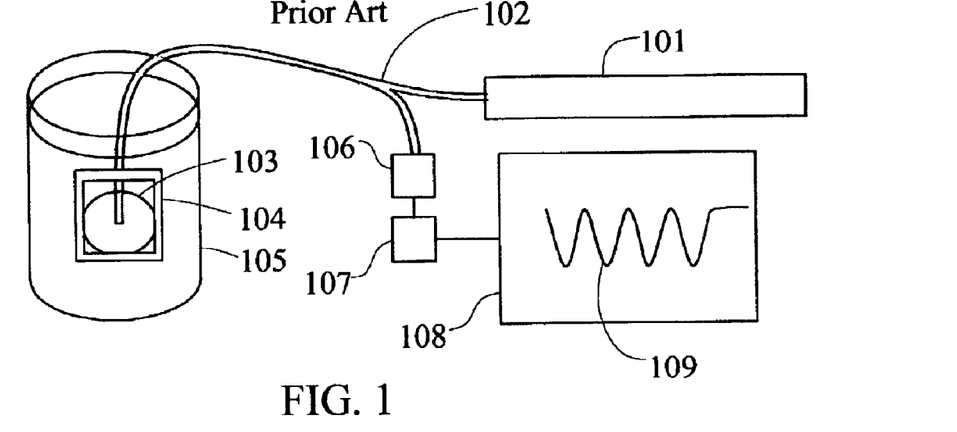
FIG. 1 shows a prior art dissolution rate monitor.

In order to use the system depicted in FIG. 1, a coated wafer is mounted in the fixture with the end of the fiber optic cable in close proximity to the wafer. The mounting procedure is done while the fixture is removed from the developer. After opening the laser shutter and starting the strip chart recorder, the fixture is immersed into the developer. The recorded signal 109, which is modulated by thin film interference effects as the film thickness decreases during development, is referred to as an "interferogram".

The analysis of the interferogram is usually done in a very simple manner. A sharp change in intensity occurs at the time when the sample is plunged into the developer; this marks the time when development starts. A development time for each peak may then be read from the chart. The film thickness at each minimum and maximum in the interferogram can be determined by counting peaks back from the end of development. The end of development may be identified because the modulation of the signal ceases. The thickness associated with each peak is then calculated as follows.

$$t = \frac{N\lambda}{4n}, \quad (1)$$

where: t=film thickness,
N=number of half cycles in peak count,
λ=wavelength, and
n=refractive index of the film.

The film thickness versus development time data then yields the desired development rate information.

In an improved version of the system shown in FIG. 1, the strip chart recorder is replaced with an automated data acquisition system. Automated peak finding and a simple method for interpolating between peaks are usually provided. Rigorous modeling of the reflectance is not usually incorporated into these systems because it is difficult to determine the incident intensity and to control other parameters.

A major disadvantage of the above system is the large quantity of developer, typically 500 ml to 2 liters, required to obtain a single set of reflectance data during development. A second disadvantage is that only one set of reflectance data can be obtained from each coated wafer. An additional disadvantage is that since two points are required to define the line, it is not possible to measure thickness below 200 nm for typical values of n and λ.

A more sophisticated prior art instrument utilizes a spectrometer to provide spectral reflectance during development. The additional data obtained provides more options for data analysis. The multi-wavelength system is also capable of measuring the thickness of a static film, but current systems have not been optimized to perform both static and dynamic functions. Also, the problems of inefficient utilization of coated substrates and developer remain.

A major improvement in capability was provided by the Perkin Elmer Development Rate Monitor (PE DRM), a commercial instrument designed to measure dissolution rates. The PE DRM simultaneously acquired data from multiple channels. The multi-channel capability is useful for simultaneously measuring dissolution rates of photoresist at different exposure dose levels. A resist-coated wafer is exposed with an array of different doses and thickness versus time data is collected during development for each zone of the array. The physical design of the PE system is very different from the simple single channel systems. The PE system utilizes a white light source to illuminate the exposure array on the wafer. The exposure array is then imaged onto a detector array. At some point in the optical system, a filter limits the radiation to quasi-monochromatic light. Large amounts of data can be collected and analyzed to provide dissolution rates corresponding to the given exposure doses. The PE multi-channel DRMs have been very popular for characterizing photoresists but are expensive. They also require large amounts of developer for each wafer and are not designed to make static measurements of film properties.

SUMMARY OF INVENTION

It is an object of the present invention to provide a thin film analyzer capable of both static and dynamic measurements.

It is a further object of the present invention to provide a thin film analyzer capable of measuring dissolution rates of thin films while consuming only small quantities of solvents.

It is also a further object of the present invention to provide a thin film analyzer capable of measuring dissolution rates of thin films in small, localized areas on a coated substrate, thereby allowing multiple, independent measurements on each substrate.

DETAILED DESCRIPTION

In the following description of a preferred embodiment of the present invention, the term "wafer" is used as an example of a substrate upon which a film may be deposited, and "developer" is used as an example of a solvent for the film of interest. Also, "photoresist" and "polymer" are used as examples of films that may be measured. The present invention is not limited to the examples recited. The film may be any transparent, or nearly transparent material in a layer sufficiently thin and smooth such that it produces optical interference effects with thickness changes. The solvent may be any solvent that exhibits essentially surface-limited dissolution with respect to the film of interest. The substrate may be any material having a surface smooth enough to allow the observation of thin film interference effects in the coated layer. The substrates for reflectance measurements may be opaque or transparent. When transparent substrates are used, the method may be adapted to use transmittance data, reflectance data, or both.

Figure 2:
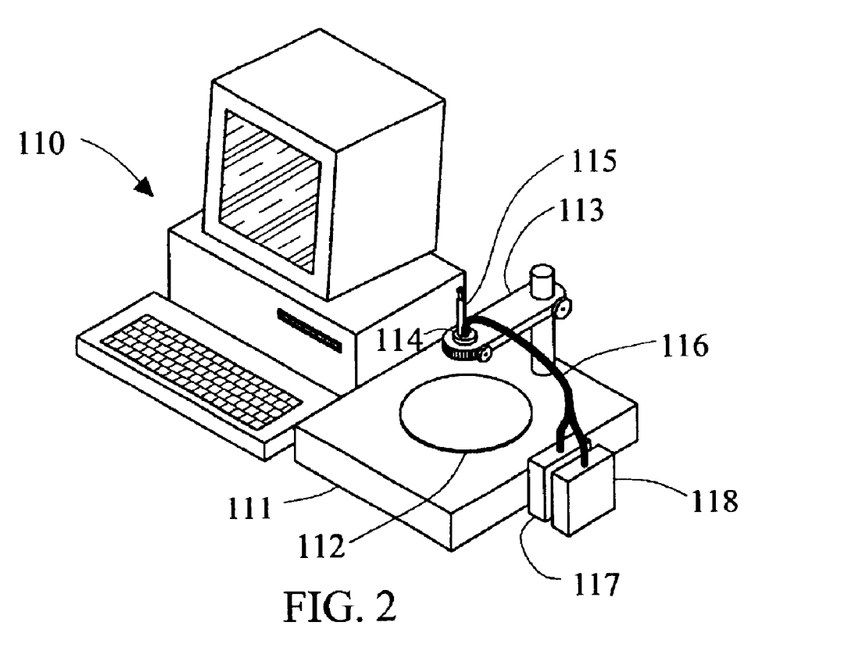
FIG. 2 is an overall view of a preferred embodiment of the present invention.

A preferred embodiment of a thin film analyzer according to the present invention is shown in FIG. 2. A computer system 110 is provided for automated data acquisition and data analysis. A rigid support base 111 provides a stable surface for a wafer 112 coated with a thin film of photoresist or polymer. The coated wafer is included in the figures to clarify the relationships between the components of the invention but is not an element of the claimed invention. A support arm 113 holds the probe head 114 with an injection syringe 115 and a bifurcated fiber optic cable 116. One branch of the bifurcated fiber optic cable goes to a polychromatic light source 117, while the other branch goes to a spectrometer 118. A variety of suitable fiber optic cables, light sources, and spectrometers are readily available from Ocean Optics, Inc. and other companies. The apparatus is shown with the support arm 113 in the fully raised position. The fully raised position facilitates loading and unloading wafers. The support arm may be fixed at various positions between fully raised and fully lowered for dry optical reflectance measurements. The support arm is moved to the fully lowered position for film dissolution rate measurements.

Figure 3:
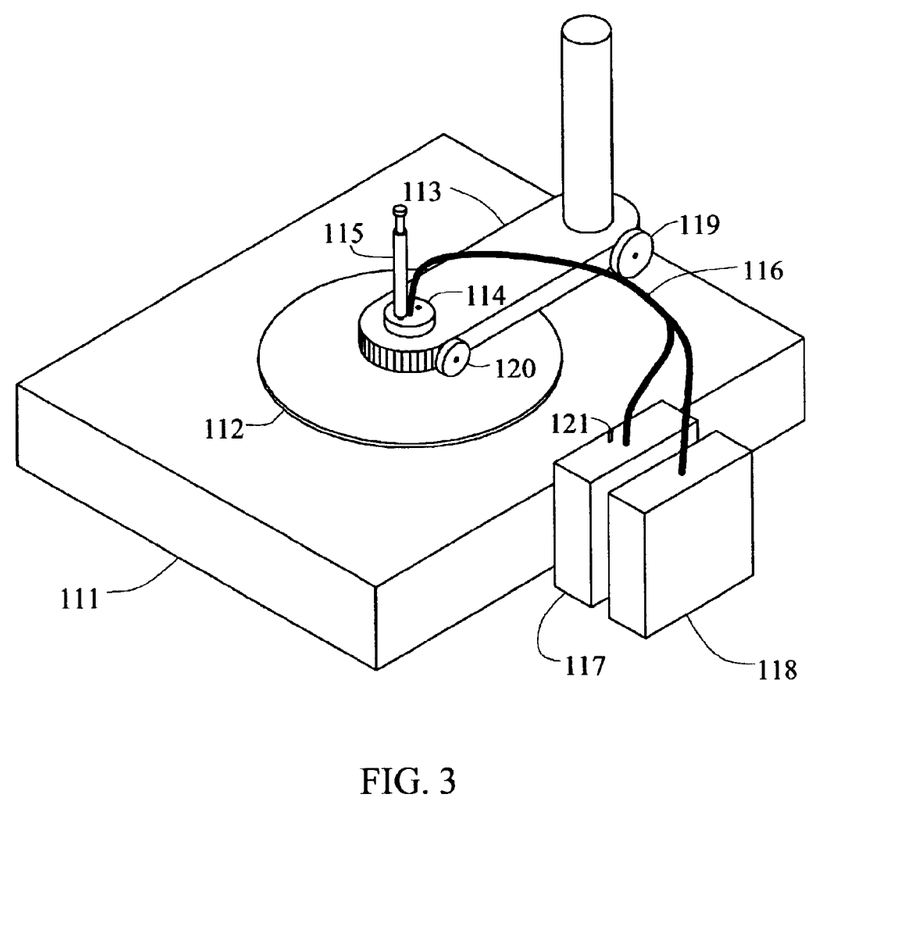
FIG. 3 is an enlarged view of the apparatus in FIG. 2, excluding the computer system.

FIG. 3 is an enlarged view of the apparatus, excluding the computer system, with the support arm 113 and the probe head 114 in the fully lowered position. The fully lowered position is used for dissolution measurements as shown later in FIG. 4 and FIG. 5. The support arm 113 is held in position with support arm locking knob 119. The probe head 114 is retained in the support arm by means of probe head locking knob 120. A shutter 121 is provided on the light source 117 so that the incident beam may be readily switched on and off. The light intensity reaching the detector can be adjusted by moving the lamp transversely to the end of the fiber pick up. This ensures that intensity adjustments can be done without changing the wavelength distribution of the light.

Figure 4:
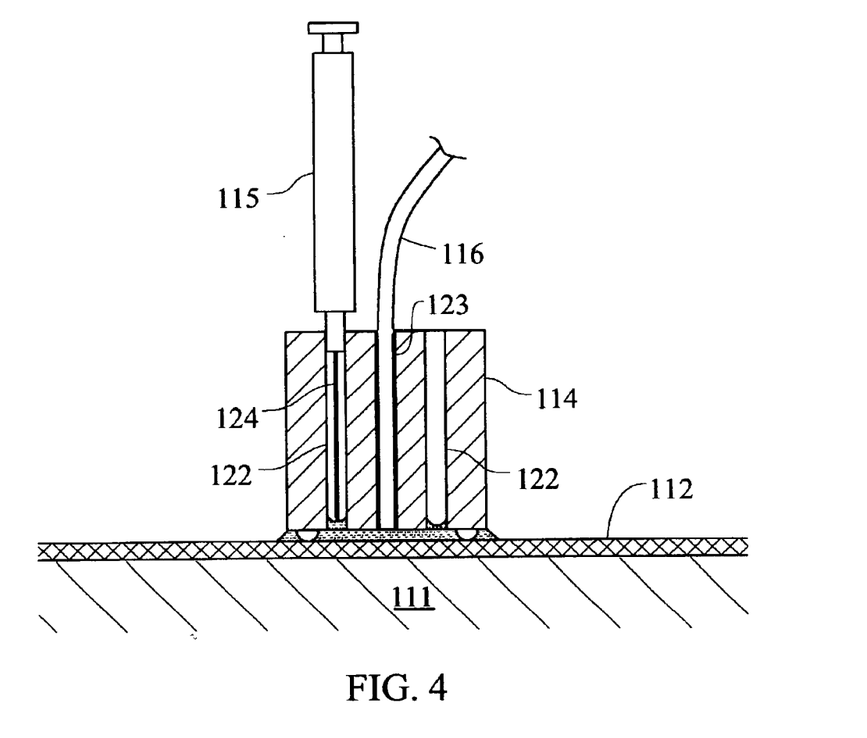
FIG. 4 is an enlarged sectional view of the probe head showing the developer injection system and the fiber optic cable but excluding the support structure shown in FIGS. 2 & 3.

FIG. 4 is an enlarged view of the probe head 114 on the surface of a coated wafer 112. The wafer is, in turn, resting on the support base 111. For clarity, the support arm and the rest of the apparatus are not shown in this figure. The probe head 114 has two apertures 122 available for dispensing and removing developer. A third aperture 123 accommodates the fiber optic cable 116. Typically a syringe 115 with a needle 124 is used to dispense the developer. Alternatively, a manual or automated micropipette may be used to dispense developer.

Figure 5:
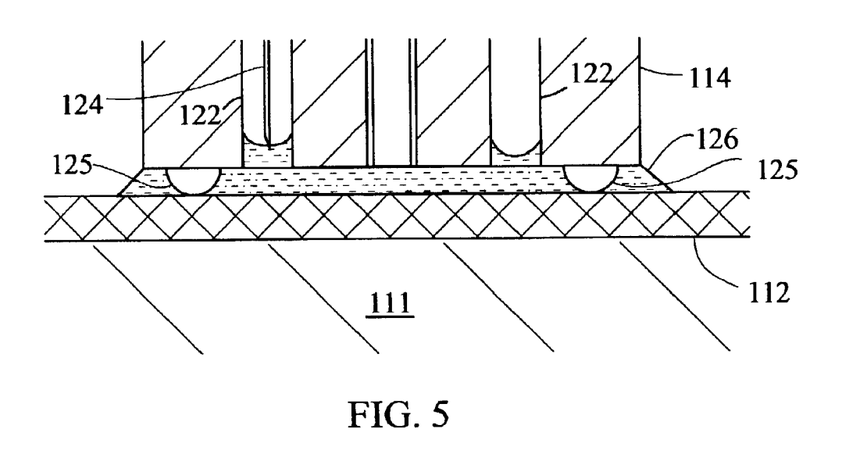
FIG. 5 is a greatly enlarged sectional view of the probe head showing the spacer bumps and developer in the gap between the probe head and the coated substrate.

FIG. 5 shows an enlarged view of the probe head 114 with spacers 125 in contact with the coated substrate 112. The gap between the probe head and the substrate is filled with developer 126. The spacer size is set to achieve a selected gap width of between 0.05 millimeters and 5 millimeters. Preferably, the gap is between 1.5 and 2.5 millimeters. The gap setting for a particular probe head may be fixed or adjustable.

Figure 6:
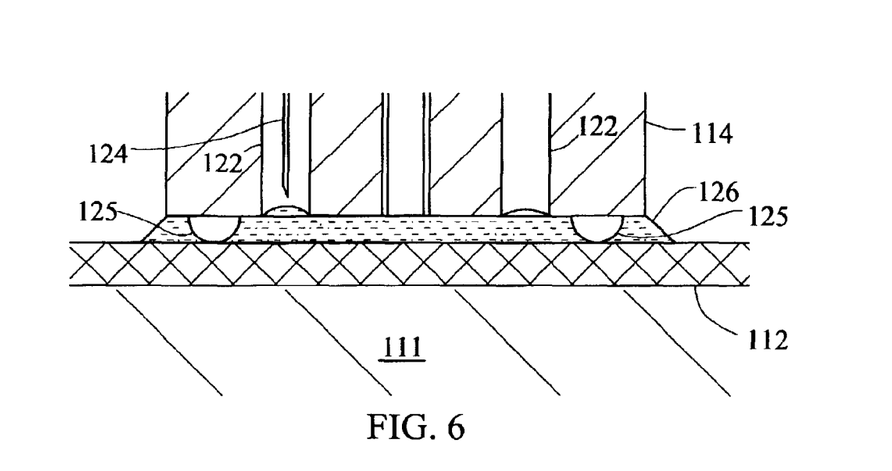
FIG. 6 is a greatly enlarged sectional view of a probe head in which the apertures are not wettable by the developer.

The probe head may be fabricated from a variety of different materials including metals, plastics, ceramics, and glasses. In one preferred embodiment the probe head is Delrin® an acetal polymer made by DuPont. The performance of the probe head is affected by the interfacial tension between the developer and the probe head. The material selected for the probe head is a factor affecting the performance of the system. It is also possible to modify the interfacial properties using chemical and physical treatments. Plasma treatments are commonly used to alter the wettability of surfaces. In FIG. 5 the menisci in the apertures 122 suggest that the developer wets the internal surfaces of the apertures. This is likely to occur when the probe head is fabricated from material inherently wettable by the developer. If the probe head is fabricated from an inherently unwettable material or the apertures are treated to render them unwettable, the developer interface will appear more like that shown in FIG. 6.

In order to measure the static thickness of a thin film coating, a bare substrate identical to the coated substrate is placed on the support base 111 directly under the probe head 114. The support arm locking knob 119 is loosened and the support arm 113 is adjusted so that the bottom surface of the probe head is at a convenient level above the coated substrate. The gap between the probe head and the substrate is not critical; it may be adjusted to accommodate other needs. Typically, the gap width is between 3 cm and 7 cm, but any gap width between 1 mm and 20 cm may be used if the light source brightness and detector sensitivity are appropriate. A spectral scan is performed with the shutter 121 closed. This dark signal is subtracted from subsequent data. A scan of the bare substrate with known optical properties allows the spectral incident intensity to be calculated. One or more scans of coated substrates may then be used for several different analytical methods known in the art. If the film is transparent (i.e. the imaginary part of the refractive index, k=0) and the Cauchy coefficients are known, the refractive index for each wavelength of the collected spectrum may be calculated. The only unknown, the film thickness, may be calculated using equation (1), if the approximate thickness is known within about a half of the wavelength of a selected interference peak. When multiple peaks are available, it is not necessary to have an approximate thickness. Alternatively, the film thickness may be incorporated as an unknown parameter in thin film reflectance models known in the art and described below. In this manner the full set of reflectance data may be utilized to obtain a statistically best fit for the calculated film thickness. The spectral data from one or more coated substrates may also be used to determine the optical constants of partially absorbing films. A variety of analytical methods yielding film thickness and optical constants from spectral reflectance data are known in the art.

Typically, dissolution rates are measured in the following manner, but variations in procedure are possible and are within the scope of the present invention. A dark scan and a reference scan with an uncoated substrate are acquired in a manner similar to that described above for thickness measurements except that the probe head 114 is lowered so that the spacers 125 make contact with the reference substrate. If it is anticipated that the film dissolution rate will be so slow that the film will not be fully dissolved during the data acquisition time, a scan of the uncoated substrate should be taken with developer in the gap between the probe head and the substrate. The developer is introduced into the gap over the reference substrate in the manner described below for the coated substrate. The reference substrate is then replaced with a coated substrate having the film to be measured. The user selects acquisition parameters such as total time of data acquisition and the number of scans per second. A syringe is prepared with 1 milliliter of developer and inserted into an aperture 122 in the probe head 114. The data acquisition is started and allowed to run a few seconds to acquire baseline data. The developer is then injected into the gap between the probe head and the coated substrate. Data acquisition continues for the preselected total acquisition time. Following the data acquisition period the developer may be removed by suction and the substrate may be rinsed with alternate injections of water and suctioning. The probe head is then raised and the substrate and probe head are further rinsed and dried as desired. The data obtained, relative reflectance as a function of wavelength and development time may be analyzed in a variety of ways to yield film dissolution rates. The film thickness at each development time may be calculated using the spectral reflectance data, as described earlier. Alternatively, the peaks in the reflectance versus development time for individual wavelengths may be analyzed in the manner described for the prior art apparatus shown in FIG. 1. The multi-wavelength data yields a nearly continuous plot of thickness versus development time.

Figure 7:
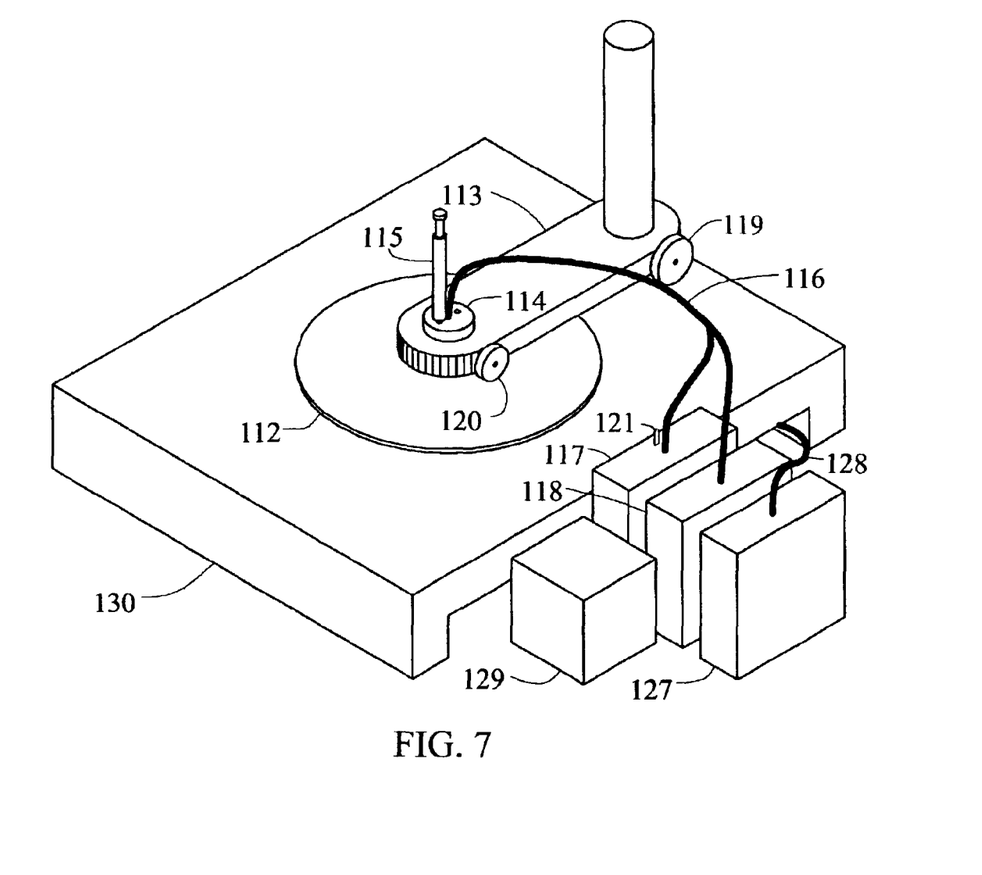
FIG. 7 is an enlarged view of a second embodiment of the present invention, excluding the computer system.
Figure 8:
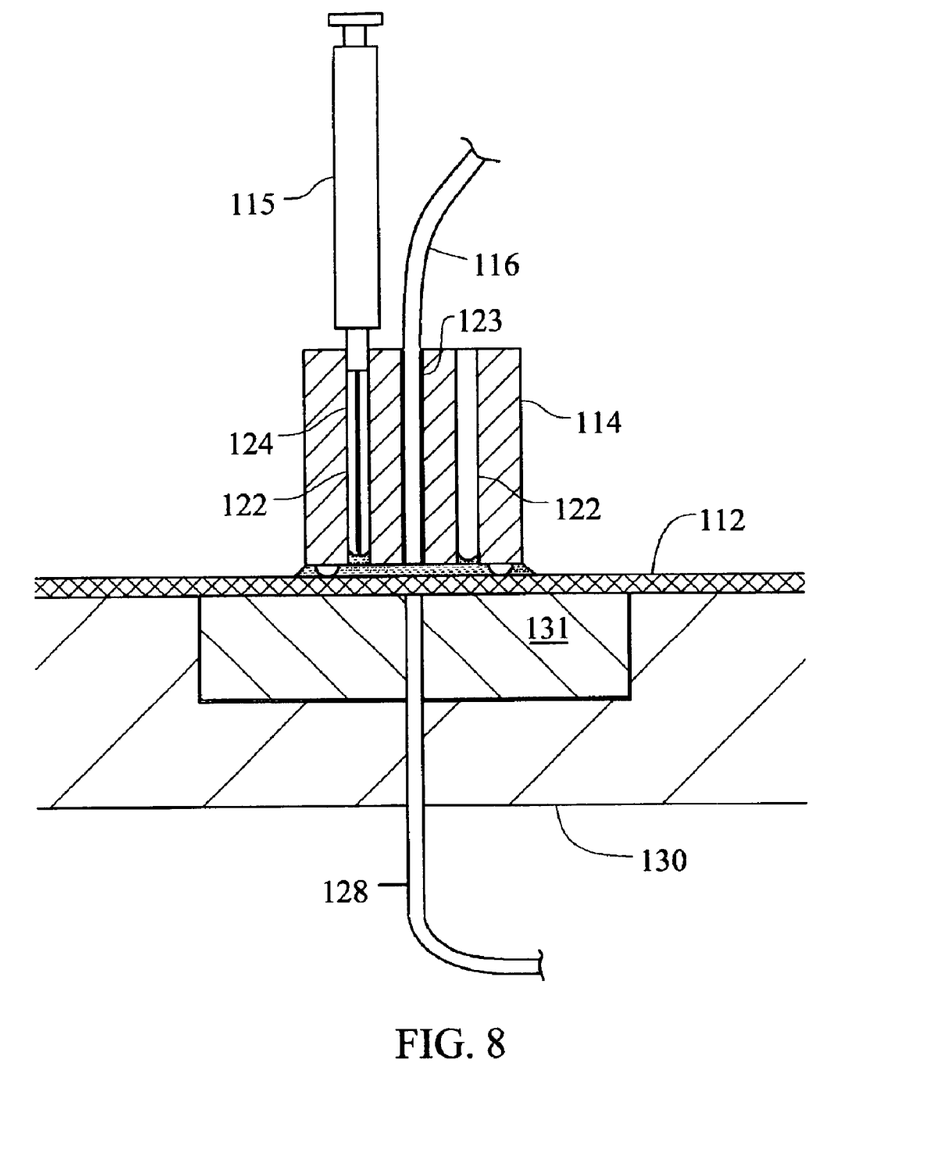
FIG. 8 is an enlarged sectional view of the system shown in FIG. 7.

A second preferred embodiment of the present invention is shown in FIG. 7. A second spectrometer 127 with a second fiber optic cable 128 is used to collect transmitted light when transparent substrates are used. A temperature controller 129 is also shown. In order to accommodate the additional fiber optic cable and an element for heating and cooling the wafer, a modified base 130 is used. FIG. 8 shows the second fiber optic cable 128 passing through the base 130 and the heating and cooling element 131 to a position below the coated substrate 112 where transmitted light may be collected. The temperature controlled base facilitates the measurement of thickness changes versus time caused by factors other than dissolution, such as the loss of a coating solvent or structural changes in the film material such as crosslinking in the case of polymer films.

The equations describing thin film reflectance are well known and available from many sources. One such reference is *Ellipsometry and Polarized Light* by R. M. A. Azzam and N. M. Bashara (Elsevier Science Publishers, 1977) and is incorporated herein by reference.

The Fresnel reflection and transmission coefficients at an interface between material "a" and material "b" for s and p polarizations are calculated as follows.

$$r_{abp} = \frac{N_b \cos\phi_a - N_a \cos\phi_b}{N_b \cos\phi_a + N_a \cos\phi_b},$$

$$r_{abs} = \frac{N_a \cos\phi_a - N_b \cos\phi_b}{N_a \cos\phi_a + N_a \cos\phi_b},$$

$$t_{abp} = \frac{2N_a \cos\phi_a}{N_b \cos\phi_a + N_a \cos\phi_b},$$

$$t_{abs} = \frac{2N_a \cos\phi_a}{N_a \cos\phi_a + N_b \cos\phi_b},$$

where r is a reflection coefficient, t is a transmission coefficient,

φ is the angle between the propagation direction and the normal,

N=n−jk is the complex refractive index, n is the real part of the refractive index, and k is the extinction coefficient.

A two by two interface matrix can then be calculated for each interface in the film stack as follows.

$$I_{ab} = (1/t_{ab}) \begin{bmatrix} 1 & r_{ab} \\ r_{ab} & 1 \end{bmatrix}.$$

A layer matrix is calculated for each layer.

$$L = \begin{bmatrix} e^{j\beta} & 0 \\ 0 & e^{-j\beta} \end{bmatrix},$$

where $$\beta = \frac{2\pi dN}{\lambda} \cos\phi$$

is the layer phase thickness, d is the film thickness, and

λ is the wavelength of the light.

The overall scattering matrix is then calculated:

$$S = \begin{bmatrix} S_{11} & S_{12} \\ S_{21} & S_{22} \end{bmatrix} = I_{01}L_1I_{12}L_2 \ldots I_{(j-1)j}L_j \ldots L_m I_{m(m+1)}.$$

The overall reflection and transmission coefficients are given by:

$$R = \frac{S_{21}}{S_{11}}, \quad T = \frac{1}{S_{11}}.$$

The above equations may be used to model a film stack. Unknown parameters in the film stack such as thicknesses and refractive indices may then be determined using well-known optimization algorithms to determine the values of the parameters that will give the best match between experimental and calculated reflectances. A preferred optimization algorithm is known as the simplex method.

EXAMPLE 1

Figure 9:
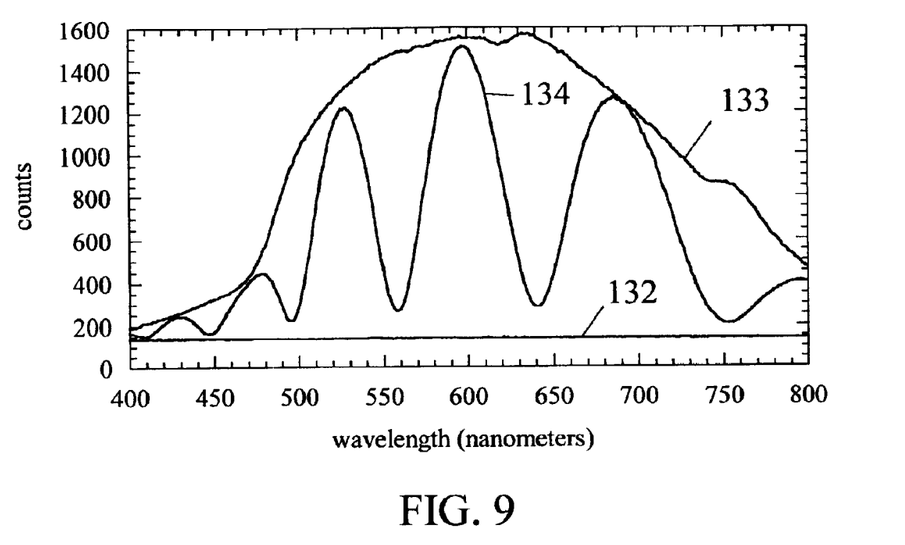
FIG. 9 shows a plot of the raw data collected in example 1.
Figure 10:
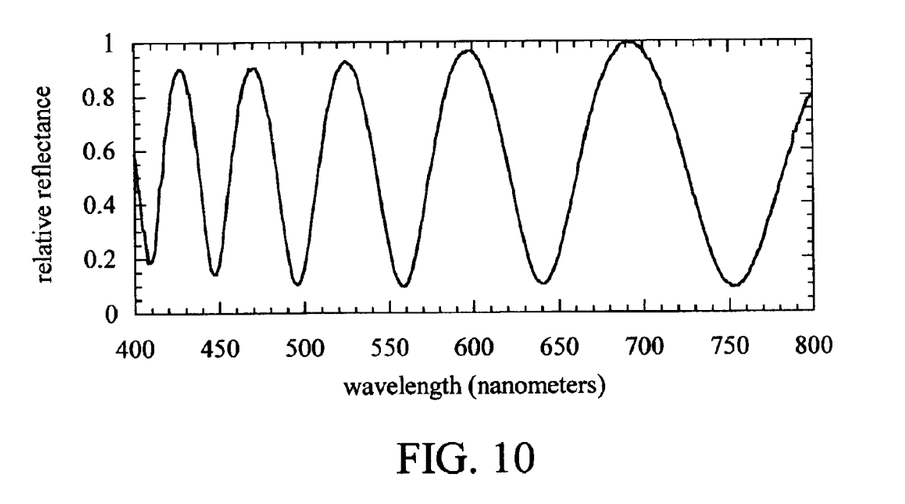
FIG. 10 is a plot of reflectance versus wavelength for the data collected in example 1.

A preferred embodiment of the present invention as shown in FIGS. 2 and 3 was used to determine the thickness of a thin film of Shipley 1813 Photoresist on a silicon wafer. The photoresist was spin coated and baked using well-known wafer processing equipment and methods. The probe head 114 was set at about 2 cm above the support base 111, and an uncoated reference wafer was placed under the probe head. A dark scan was taken with the light source shutter 121 closed and a reference scan with the shutter open. The resulting scans are shown in FIG. 9 where the dark scan is identified as 132 and the reference scan is marked 133. The uncoated reference wafer was then replaced with the coated wafer and scanned, yielding the curve identified as 134. After subtracting the dark signal from the reference and film signals, the corrected film signal was divided by the reference signal to yield relative reflectance as shown in FIG. 10. An analysis of the peaks based on the relationship in equation (1) gives the film thickness, 1370 nm.

EXAMPLE 2

Figure 11:
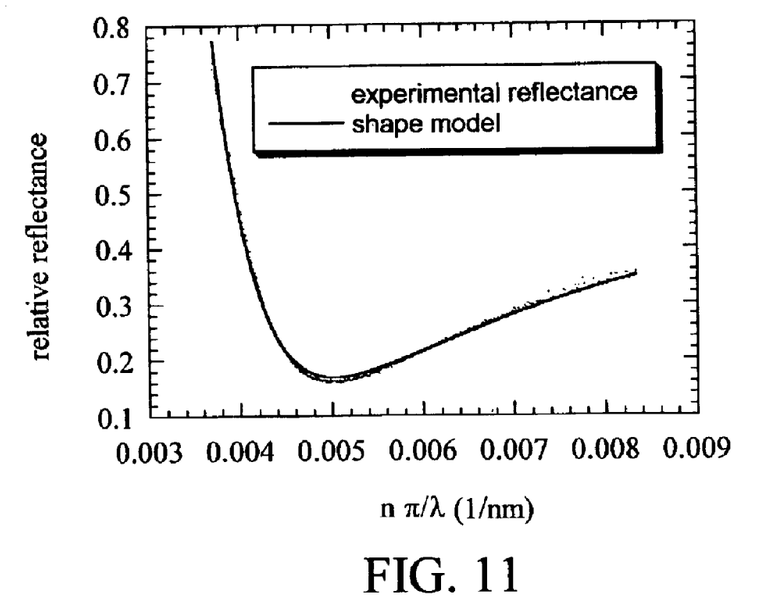
FIG. 11 is a plot of reflectance versus $n\pi/\lambda$ for the data collected in example 2.

The apparatus shown in FIGS. 2–5 was used to measure the thickness of a thin film of poly(hydroxystyrene) on a silicon wafer. A dark scan and a reference scan were acquired as in example 1, and reflectance versus wavelength was calculated as before. In this case the experimental reflectance data were plotted versus $n\pi/\lambda$, as shown in FIG. 11, to facilitate an analysis based on the shape of the curve rather than on peak locations. The calculated thickness using the shape analysis was 95.6 nm. FIG. 11 shows the agreement between the experimental reflectance values and the curve produced by the fitted shape model.

EXAMPLE 3

Figure 12:
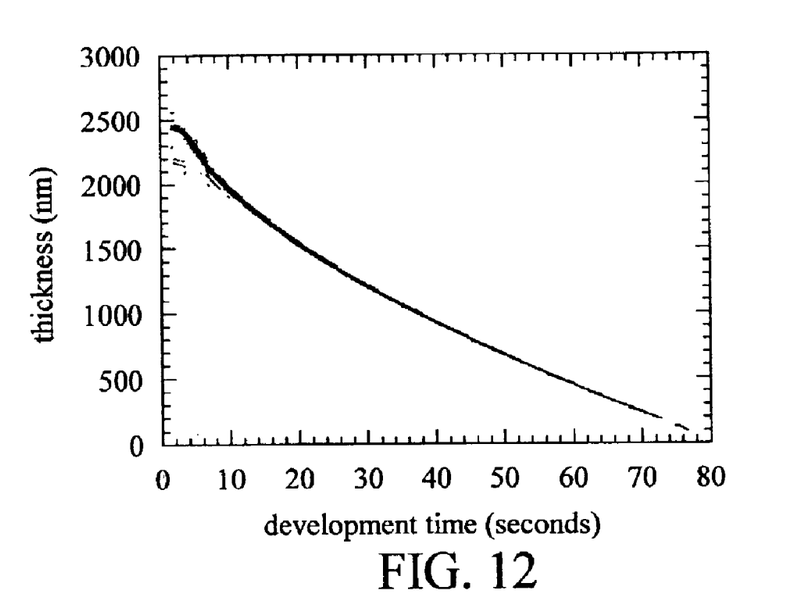
FIG. 12 is a plot of thickness versus development time calculated using the data collected in example 3.

The apparatus shown in FIGS. 2–5 was used to measure the dissolution rate of an ultraviolet exposed, 1279 nm thick film of Shipley Microposit® 1813 photoresist in Shipley Microposit® 319 Developer. A reference wafer was positioned under the probe head 114 with the spacers 125 in contact with the wafer surface. A dark scan and a reference scan were taken. The reference wafer was replaced with the coated wafer and data collection parameters were selected. A total acquisition time of 80 seconds was chosen based on an estimated dissolution rate. One ml of developer was drawn into a syringe. The data collection was started, and the system was allowed to collect approximately twenty base-line points before injecting the developer. After the specified development time, the developer was removed, and the wafer was rinsed and dried. Approximately 5400 spectra similar to that shown in FIG. 8 were collected as the film dissolved. Analysis using conventional techniques gave the thickness versus development time curve shown in FIG. 12.

What is claimed is:

1. An apparatus for optically analyzing a thin film on a substrate comprising:
   (a) a base capable of supporting said substrate,
   (b) means for generating radiant energy,
   (c) a first means for detecting radiant energy,
   (d) a probe head comprising:
      means for dispensing liquid,
      means for directing radiant energy from said means for generating radiant energy toward said substrate,
      a first means for directing radiant energy from said substrate to said first means for detecting radiant energy,
   (e) means for supporting said probe head proximate to said substrate, thereby forming a gap between said probe head and said substrate.

2. The apparatus of claim 1 wherein said gap is between 0.05 mm and 5 mm.

3. The apparatus of claim 2 wherein said gap is between 1.5 mm and 2.5 mm.

4. The apparatus of claim 1 wherein said base comprises a heater.

5. The apparatus of claim 1 wherein said base comprises a cooler.

6. The apparatus of claim 1 wherein said means for directing radiant energy from said means for generating radiant energy toward said substrate comprises a first set of optical fibers having a first end and a second end wherein said first end is connected to said means for generating radiant energy and said second end is connected to said probe head, thereby causing radiant energy to transit said gap and illuminate said substrate.

7. The apparatus of claim 6 wherein said first means for directing radiant energy from said substrate to said first means for detecting radiant energy comprises a second set of optical fibers having a first end and a second end wherein said first end of said second set of optical fibers is connected to said base and said second end of said second set of optical fibers is connected to said first means for detecting radiant energy, thereby directing transmitted radiant energy to said first means for detecting radiant energy.

8. The apparatus of claim 6 wherein said means for directing radiant energy from said substrate to said first means for detecting radiant energy comprises a second set of optical fibers having a first end and a second end wherein said first end of said second set of optical fibers is connected to said probe head and said second end of said second set of optical fibers is connected to said first means for detecting radiant energy, thereby directing reflected radiant energy to said first radiant energy detector.

9. The apparatus of claim 8 wherein said gap is 0.05 mm–5 mm.

10. The apparatus of claim 8 wherein said first end of said second set of optical fibers is bundled with said second end of said first set of optical fibers, thereby forming a bifurcated fiber optic cable.

11. The apparatus of claim 9 wherein said means for generating radiant energy is a polychromatic light source.

12. The apparatus of claim 11 wherein said first means for detecting radiant energy is a first spectrometer.

13. The apparatus of claim 12 further comprising a second spectrometer and a third set of optical fibers having a first end and a second end, wherein said first end of said third set of optical fibers is connected to said base and said second end of said third set of optical fibers is connected to said second spectrometer, thereby directing transmitted radiant energy to said second spectrometer.

14. The apparatus of claim 13 wherein said means for dispensing liquid into said gap comprises a syringe.

15. The apparatus of claim 13 wherein said means for dispensing liquid into said gap comprises a pipette.

16. A method for analyzing a thin film comprising the steps of:

(a) providing a substrate coated with a thin film, (b) providing the apparatus of claim 1, (c) positioning said substrate on said base, (d) positioning said probe head proximate to said substrate, thereby forming said gap between said probe head and said substrate, (e) injecting liquid into said gap, (f) directing polychromatic light through said gap toward said substrate, (g) directing reflected light from said substrate to said means for detecting radiant energy, (h) analyzing the signal produced by said means for detecting radiant energy to yield information related to the properties of said thin film.

* * * * *